United States Patent [19]

Robba et al.

[11] 4,035,371

[45] July 12, 1977

[54] PROPIONIC ACID DERIVATIVES

[75] Inventors: Max Fernand Robba, Paris; Denise Jeanne Claude Duval, Yvelines, both of France

[73] Assignee: Innothera, Arcueil, France

[21] Appl. No.: 651,223

[22] Filed: Jan. 22, 1976

Related U.S. Application Data

[62] Division of Ser. No. 489,545, July 18, 1974, which is a division of Ser. No. 150,747, June 7, 1971, Pat. No. 3,865,842.

[30] Foreign Application Priority Data

June 12, 1970 France ............................ 70.21679

[51] Int. Cl.$^2$ ........................................ C07D 409/12

[52] U.S. Cl. ...................... 260/293.57; 260/326.34; 260/330.5

[58] Field of Search .............. 260/247.1 P, 293.57, 260/330.5, 326.34

[56] References Cited

U.S. PATENT DOCUMENTS

| | | | |
|---|---|---|---|
| 2,517,826 | 8/1950 | Avakian et al. | 260/330.5 |
| 2,857,383 | 10/1958 | Voegtli | 260/330.5 |
| 2,916,495 | 12/1959 | Edgerton | 260/330.5 |

*Primary Examiner*—G. Thomas Todd
*Attorney, Agent, or Firm*—Stevens, Davis, Miller & Mosher

[57] ABSTRACT

β-[Benzo(b)thienyl-3] propionic acid derivatives in the form of their amino esters (and salts thereof) are prepared. These compounds have spasmolytic, vasodilatatric, antiserotanic and local anaesthetic activity.

6 Claims, No Drawings

PROPIONIC ACID DERIVATIVES

This is a division of application Ser. No. 489,545, filed 7/18/74 which is a division of U.S. application Ser. No. 150,747 filed 6/7/71, now U.S. Pat. No. 3,865,842 granted 2/11/73.

The invention relates to $\beta$-[benzo(b)thienyl-3] propionic acid derivatives and the amino esters of these derivatives.

The compounds of the invention correspond to the following formula:

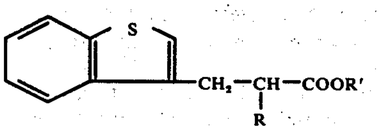

wherein

R represents an allyl, phenyl, benzyl, thenyl, tetrahydrofurfuryl or tetrahydropyrannyl-methyl radical and R' represents a hydrogen atom or the group

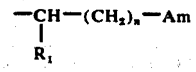

wherein $R_1$ represents a hydrogen atom or a linear or branched alkyl having 1 to 3 carbon atoms Am represents the radical of a dialkylamine of which the alkyls have 1 to 4 carbon atoms or the radical of an cyclic amine having 5, 6 or 7 members which may include a supplementary hetero atom, and

*n* is 1 or 2.

The cyclic amine radical may be particularly that of pyrrolidine, piperidine, cyclohexamethylene-imine or morpholine.

The invention includes the salts which give amino-esters with pharmaceutically acceptable mineral or organic acids as well as the quaternary ammonium derivatives of these amino-esters, and the racemic and optically active forms of the acids and amino-esters.

The derivatives of $\beta$[benzo(b)thienyl-3] propionic acid may be prepared, according to the invention, from 3-chloromethyl-benzo(b) thiophene by malonic synthesis.

One may work, in particular, in the following manner: the 3-chloromethyl-benzo (b) thiophene is condensed with a malonic ester carrying, in 2-position, the radical R (compound III) by warming to reflux in ethanol in the presence of sodium ethylate.

After hydrolysis in an aqueous hydrochloric acid medium there is obtained a malonic ester carrying in 2-position, as well as the radical R, the radical [benzo(b) thienyl-3] methyl (compound IV) which is extracted with diethyl ether and distilled.

By prolonged heating under reflux in a solution of potassium in benzyl alcohol, the malonic esters (IV) are saponified ad decarboxylated. After dilution with water and acidification, there are obtained the $\beta$-[benzo(b)thienyl-3] propionic acids (Compounds I) which may be purified by distillation in vacuo and recrystallisation.

The malonic ester used is, for preference, ethyl malonate.

In this case the reaction scheme is the following:

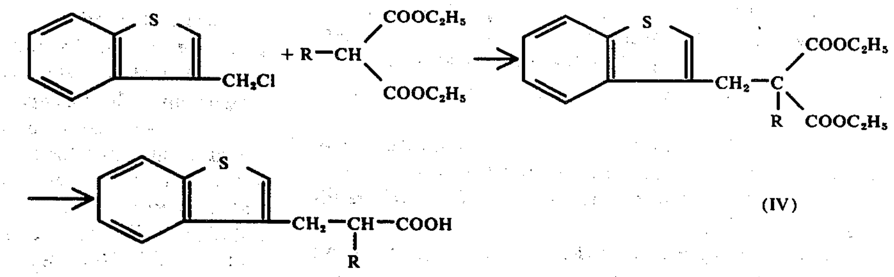

(IV)

The aminated esters (compounds II) of the $\beta$-[benzo(b) thienyl-3] propionic acids (compounds I) may be prepared by heating the acids to reflux in isopropanol with the amino-alcohol chlorides of the formula

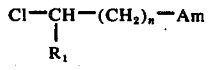

wherein $R_1$, *n* and Am have the meanings given above.

The amino esters are thus obtained in the form of their hydrochlorides. The amino-esters (bases) are oils.

To obtain them in the form of organic acid salts the hydrochloride may be treated in aqueous solution with soda, the amino-ester extracted with the aid of an organic solvent, the solvent eliminated in vacuo, the residue dissolved in acetone, 1.5 equivalents of the selected organic acid added and the mixture refluxed for 15 to 30 minutes. The salt crystallises on cooling.

The following Examples illustrate the present invention:

EXAMPLE 1 a. Allyl[(benzo(b) thienyl-3) methyl]malonate ethyl ester

A solution of 23 g of sodium and 200 g of 2-allyl malonate ethyl ester in 600 cc of absolute ethanol is heated to reflux for 1 hour. It is slightly cooled and a solution of 181.5 g of 3-chloromethyl-benzothiophene in 100 cc of absolute alcohol is poured in. It is heated to reflux, with stirring, for 17 hours. It is poured into 1 liter of water, acidified with hydrochloric acid and extracted with ether. It is dried over sodium sulphate, the solvent eliminated and it is distilled in vacuo. A yellow oil is obtained. B. Pt. $_5$ = 240°–250°. Yield 70%.

b. $\alpha$-allyl-$\beta$-[benzo(b)thienyl-3]propionic acid

A solution of 300 g of allyl [(benzo(b) thienyl-3)-methyl]malonate ethyl ester and 97 g of potassium in 3.5 liters of benzyl alcohol is heated to reflux for 15 hours. The solvent is distilled in vacuo, the residue poured into 2 liters of water, acidified with hydrochloric acid and extracted with benzene. It is dried over sodium sulphate, the solvent eliminated and the residue distilled in vacuo. A yellow oil is obtained. B. pt. $_3$ = 215°. Yield 80%.

EXAMPLES 2–6 a. By operating as in Example 1(a) one obtains in the form of yellow distillable oils the malonic esters indicated below:

phenyl[(benzo(b)thienyl-3)-methyl]malonate ethyl ester, B.pt$_{12}$. = 235°–245° — Yield: 72% benzyl[(benzo(b)thienyl-3)-methyl]malonate ethyl ester, B.pt.$_6$ = 250°–260° — Yield: 75%

(thenyl-2')[(benzo(b)thienyl-3')-methyl]malonate ethyl ester, B.pt$_8$. = 280°–290° — Yield: 80%

(tetrahydro-furfuryl)[(benzo(b)thienyl-3')-methyl]-malonate ethyl ester, B.pt$_5$. = 238°–246° — Yield: 80%

(tetrahydropyrannyl-methyl)[(benzo(b)thienyl-3)-methyl]malonate ethyl ester — B.pt$_5$. = 247°–253° — Yield: 65%.

b. From the listed malonic esters, and operating as in Example 1(b) there are obtained the following β-[benzo(b) thienyl-3]propionic acids in the form of distillable oils or solids:

α-phenyl β-[benzo(b)thienyl-3]propionic acid; white crystals; m.p 120°, B.p.$_9$ = 260°–263°; cristallisable in a mixture of 1/1 acetonitrile and hexane — Yield: 70%.

α-benzyl β-[benzo(b)thienyl-3]propionic acid; white solid m.p. 116°; B.p.$_5$ = 245°–255°; cristallisable in a mixture of 2 liters of hexane and 150 cc of ethyl acetate — Yield: 80%.

α-(thenyl-2)β-[benzo(b)thienyl-3]propionic acid; white crystals; m.p. 85°; b.p.$_9$ = 290°–300°; cristallisable in a mixture (4/1) of hexane and ethyl acetate — Yield: 75%.

α-tetrahydrofurfuryl β-[benzo (b) thienyl-3] propionic acid; white crystals; m.p. 116°; b.p. = 240°–243°; cristallisable in a mixture (4/1) of hexane and ethyl acetate — Yield; 80%.

α-(tetrahydropyrannyl-methyl)β-[benzo (b) thienyl-3]propionic acid; white crystals; m.p. 100°; cristallisable in a mixture (1/2) of ethyl acetate and hexane — Yield: 50%.

EXAMPLE 7

N,N-diethylamino ethyl ester of α-phenyl-β-[benzo (b) thienyl-3]propionic acid and its oxalate There is heated to reflux for 17 hours a solution of 5 g of α-phenyl-β-[benzo (b) thienyl-3]propionic acid and 2.4 g of N,N-diethylamino-chloroethane in 60 cc isopropanol. It is evaporated to dryness in vacuo, the residue taken up in a saturated aqueous solution of sodium carbonate and extracted with chloroform. The solvent is dried over sodium sulphate and then eliminated. The residue is dissolved in 50 cc acetone, the solution is filtered and then added to a solution of 3 g oxalic acid in 20 cc acetone. It is heated to reflux for 30 minutes and separated after cooling. It is recrystallised in a mixture of 1/1 diethyl ether and absolute ethanol. White crystals are obtained. M.p. 110°.

Yield 65%.

In Tables I, II, III, IV and V set out below there are identified the amino ester salts of β-[benzo(b)thienyl-3]propionic acids prepared in a similar fashion, the salt of Example 7 being assigned the number 13.

TABLE I

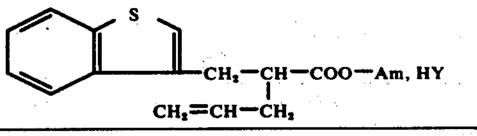

| No. | Am | Nature of the salt-forming acid HY | Melting Point ° C | Yield % | Solvent of cristallisation |
|---|---|---|---|---|---|
| 1 | 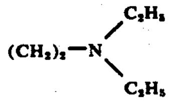 | citric acid | 97 | 60 | acetonitrile |
| 2 | 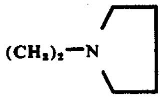 | oxalic acid | 98 | 65 | acetonitrile |
| 3 | 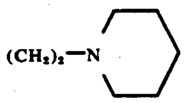 | citric acid | 85 | 75 | acetonitrile |
| 4 | 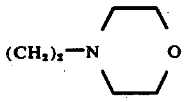 | oxalic acid | 110 | 70 | acetonitrile |
| 5 | 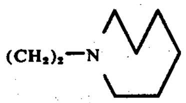 | oxalic acid | 120 | 65 | acetonitrile |
| 6 | 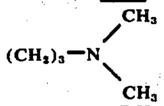 | oxalic acid | 115 | 60 | acetonitrile |
| 7 | 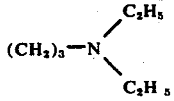 | citric acid | 85 | 70 | acetonitrile (1) plus ethyl ether (1) |

TABLE I-continued

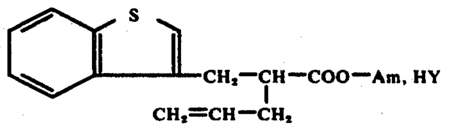

| No. | Am | Nature of the salt-forming acid HY | Melting Point ° C | Yield % | Solvent of cristallisation |
|---|---|---|---|---|---|
| 8 | 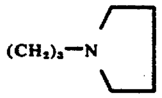 | citric acid | 86 | 75 | acetonitrile |
| 9 | 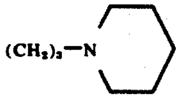 | oxalic acid | 102 | 65 | acetonitrile |
| 10 | 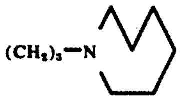 | oxalic acid | 100 | 60 | acetonitrile (1) plus ethyl ether (1) |
| 11 | 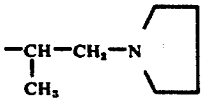 | oxalic acid | 92 | 65 | acetonitrile |

TABLE II

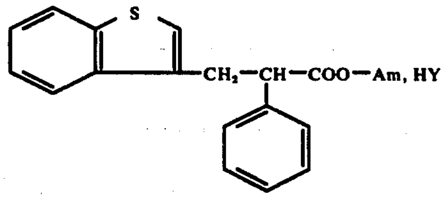

| No. | Am | Nature of the salt forming acid HY | Melting Point ° C | Yield % | Solvent of cristallisation |
|---|---|---|---|---|---|
| 12 | 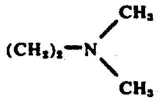 | oxalic acid | 150 | 70 | acetonitrile (1) plus ethyl ether (1) |
| 13 | 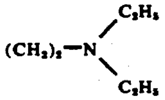 | oxalic acid | 110 | 65 | absolute ethanol (1) plus ethyl ether (1) |
| 14 | 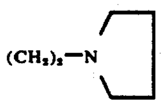 | citric acid | 85 | 65 | acetonitrile |
| 15 | 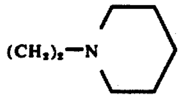 | oxalic acid | 130 | 70 | absolute ethanol (1) plus ethyl ether (1) |
| 16 | 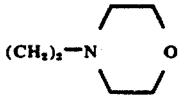 | oxalic acid | 135 | 75 | ethyl alcohol 95% |
| 17 | 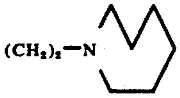 | oxalic acid | 140 | 70 | absolute ethanol (1) plus ethyl ether (1) |
| 18 | 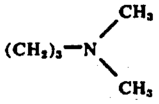 | oxalic acid | 168 | 60 | absolute ethanol (1) plus ethyl ether (1) |

TABLE II-continued

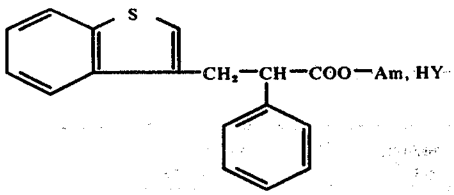

| No. | Am | Nature of the salt forming acid HY | Melting Point ° C | Yield % | Solvent of cristallisation |
|---|---|---|---|---|---|
| 19 | 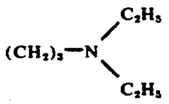 | citric acid | 95 | 65 | acetonitrile |
| 20 | 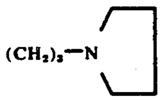 | oxalic acid | 103 | 65 | absolute ethanol (1) plus ethyl ether (1) |
| 21 | 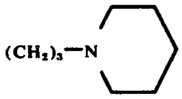 | oxalic acid | 141 | 70 | ethyl alcohol 95% (1) plus ethyl ether (1) |
| 22 | 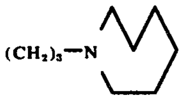 | oxalic acid | 101 | 65 | acetonitrile |
| 23 | 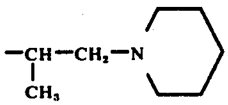 | citric acid | 90 | 70 | acetonitrile (1) plus ethyl ether (1) |

TABLE III

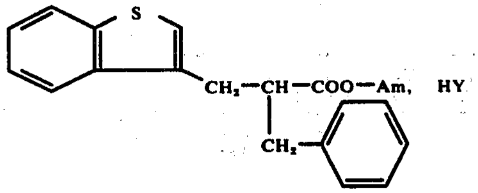

| No. | Am | Nature of the salt forming acid HY | Melting Point ° C | Yield % | Solvent of cristallisation |
|---|---|---|---|---|---|
| 24 | 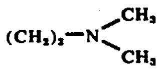 | oxalic acid | 133 | 75 | acetonitrile (1) + ethyl ether (1) |
| 25 | 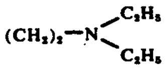 | citric acid | 115 | 70 | acetonitrile |
| 26 | 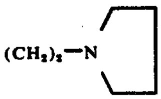 | citric acid | 100 | 60 | acetonitrile |
| 27 | 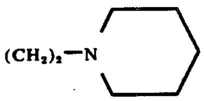 | citric acid | 85 | 65 | acetonitrile |
| 28 | 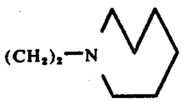 | oxalic acid | 136 | 70 | acetonitrile |
| 29 | 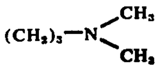 | oxalic acid | 118 | 75 | acetonitrile |

TABLE III-continued

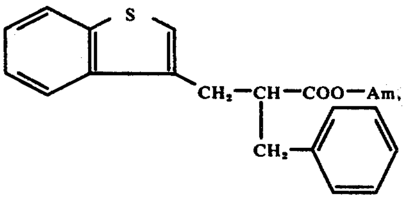

| No. | Am | Nature of the salt forming acid HY | Melting Point ° C | Yield % | Solvent of cristallisation |
|---|---|---|---|---|---|
| 30 | 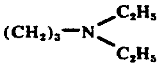 | citric acid | 87 | 80 | acetonitrile |
| 31 | 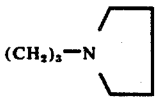 | oxalic acid | 113 | 75 | acetonitrile (1) + ethyl ether (1) |
| 32 | 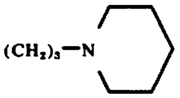 | citric acid | 85 | 70 | acetonitrile (1) + ethyl ether (1) |
| 33 | 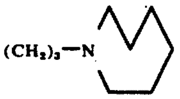 | oxalic acid | 128 | 75 | acetonitrile (1) + ethyl ether (1) |
| 34 | 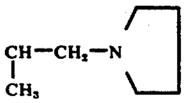 | citric acid | 80 | 65 | acetonitrile |

TABLE IV

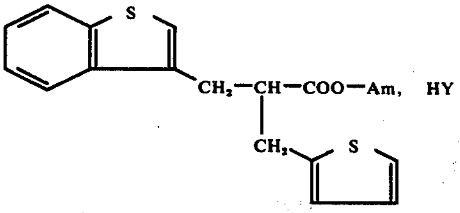

| No. | Am | Nature of the salt forming acid HY | Melting Point ° C | Yield % | Solvent of cristallisation |
|---|---|---|---|---|---|
| 35 | 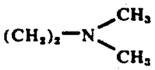 | oxalid acid | 133 | 70 | acetonitrile |
| 36 | 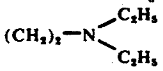 | citric acid | 111 | 75 | acetonitrile (1) + ethyl ether (1) |
| 37 | 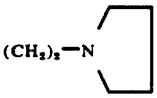 | citric acid | 105 | 70 | acetonitrile (1) + ethyl ether (1) |
| 38 | 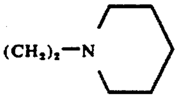 | citric acid | 88 | 80 | acetonitrile (1) + ethyl ether (1) |
| 39 | 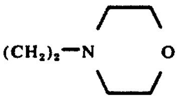 | oxalic acid | 160 | 65 | acetonitrile (1) + ethyl ether (1) |
| 40 | 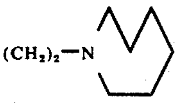 | oxalic acid | 133 | 70 | absolute ethanol (1) + ethyl ether (1) |

TABLE IV-continued

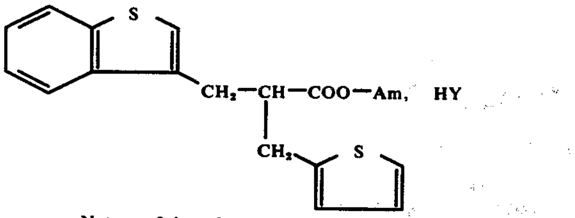

| No. | Am | Nature of the salt forming acid HY | Melting Point ° C | Yield % | Solvent of cristallisation |
|---|---|---|---|---|---|
| 41 | 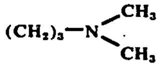 | oxalic acid | 115 | 70 | acetonitrile |
| 42 | 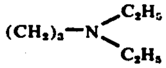 | citric acid | 85 | 75 | acetonitrile |
| 43 | 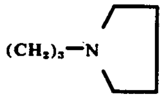 | citric acid | 85 | 80 | acetonitrile (1) + ethyl ether (1) |
| 44 | 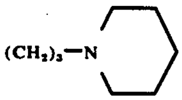 | oxalic acid | 135 | 75 | absolute ethanol (1) + ethyl ether (1) |
| 45 | 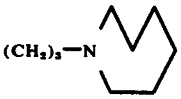 | citric acid | 86 | 70 | acetonitrile |
| 46 | 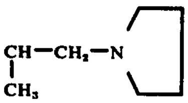 | citric acid | 78 | 75 | acetronitrile |

TABLE V

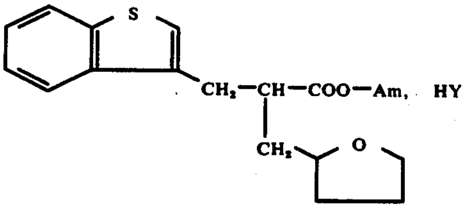

| No. | Am | Nature of the salt forming acid HY | Melting Point ° C | Yield % | Solvent of cristallisation |
|---|---|---|---|---|---|
| 47 | 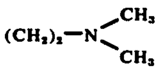 | oxalic acid | 110 | 80 | acetonitrile |
| 48 | 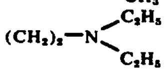 | citric acid | 90 | 75 | acetonitrile (1) + ethyl ether (1) |
| 49 | 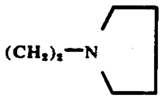 | oxalic acid | 120 | 75 | acetonitrile |
| 50 | 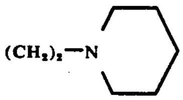 | oxalic acid | 140 | 70 | absolute ethanol (1) + ethyl ether (1) |
| 51 | 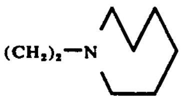 | oxalic acid | 124 | 75 | acetonitrile |
| 52 | 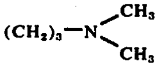 | oxalic acid | 89 | 65 | acetonitrile |
| 53 | 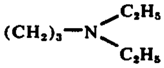 | citric acid | 83 | 75 | acetonitrile |

TABLE V-continued

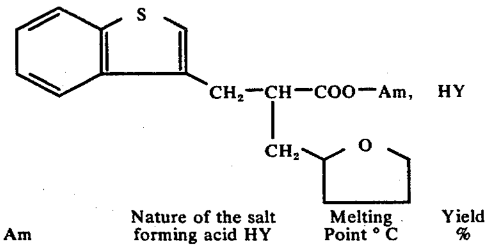

| No. | Am | Nature of the salt forming acid HY | Melting Point ° C | Yield % | Solvent of cristallisation |
| --- | --- | --- | --- | --- | --- |
| 54 | 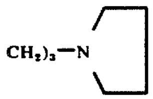 | oxalic acid | 100 | 70 | acetonitrile |
| 55 | 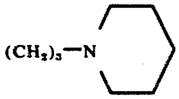 | oxalic acid | 98 | 75 | acetonitrile |
| 56 | 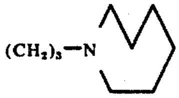 | oxalic acid | 95 | 70 | acetonitrile |

The salts of amino ester derivatives of β-[benzo(b) thienyl-3]propionic acid have been made the subject of a pharmacological study showing their spasmolytic, vasodilatatric, antiserotonic and local anaesthetic activity.

1. Acute Toxicity

The acute toxicity of the amino ester derivatives of β-[benzo(b) thienyl-3]propionic acid have been studied in the mouse by intraperitoneal and oral routes, the products being administered in an isotonic solution of sodium chloride, 0.9%, or in suspension in a dilute aqueous solution of carboxymethyl cellulose.

The calculation of the DL50 has been effected according to the method of MILLER and TAINTER (MILLER. L. C., TAINTER M. L. - Proc. Soc. Exptl. Biol. Med. 1944–57–261,264).

The results obtained are set out in Table IV for the compounds used by way of example.

TABLE VI

Acute toxicity in the mouse

| Compound No. | Route | Conc. g/100 ml of solution or suspension | DL 50 (in mg/kg) |
| --- | --- | --- | --- |
| 5 | i.p. | 1.0 | 150 ± 17 |
| 6 | i.p. | 1.0 | about 120 |
| | i.p. | 2.0 | 210 ± 10 |
| 7 | v.o. | 5.0 | 1290 ± 80 |
| 11 | i.p. | 1.0 | 270 ± 59 |
| 37 | i.p. | 2.0 | 320 ± 21 |
| 42 | i.p. | 2.0 | 240 ± 18 |
| 43 | i.p. | 1.0 | 160 ± 11 |
| 49 | i.p. | 2.0 | 140 ± 9 |
| | v.o. | 5.0 | about 650 |
| 50 | i.p. | 1.0 | 122 ± 12 |
| 51 | i.p. | 1.0 | 121 ± 10 |
| 53 | i.p. | 1.0 | 145 ± 9 |
| | v.o | 5.0 | 1150 ± 78 |
| 54 | i.p. | 1.0 | 100 ± 12 |
| | v.o. | 5.0 | 400 ± 27 |
| 55 | i.p. | 1.0 | 85 ± 12 |
| | v.o | 2.5 | about 450 |

2. Spasmolytic Activity

The spasmolytic activity has been studied on isolated organs maintained in survival in a Tyrode solution aerated and heated to 38° for the rat duodenum, to 33° for the isolated ileum of the guinea pig, according to the technique of Magnus (Magnus R, Archiv. Ges. Physiol. - 1905 - 180 - 1.71).

a. To show activity of the papaverinic type, the contracturant used is barium chloride acting on the isolated rat duodenum.

The average activity of the substances studied has been effected by determining graphically their DE 30 and DE 50 these being expressed in μg for 20 ml of bath.

The results obtained with certain selected compounds taken by way of example and indicated in Table VII show that the derivatives of β-[benzo(b)thienyl-3]propionic acid possess a spasmolytic activity of papaverinic type.

This activity is equal or clearly superior to that of papaverine hydrochloride, this reference substance having a DE 50 varying generally between 60 and 80 μg/20 ml of bath in the experimental conditions defined above.

b. To show activity of atropinic type the contracturant used is acetylcholine chloride acting on the isolated ileum of the guinea-pig.

The average activity of the substances studied has been similarly researched by determining graphically their DE 30 and DE 50, these being expressed in μg/20 ml of bath.

The results obtained with certain compounds selected by way of example and indicated in Table VII show that the derivatives studied possess a weak atropinic activity, the DE 50 of atropine sulphate being equal to or less than 0.1μg/20 ml of bath in the experimental conditions defined above.

TABLE VII

Spasmolytic activity in vitro

| Compound No. | Spasmolytic activity | | | |
| --- | --- | --- | --- | --- |
| | Papaverinic type | | Atropinic type | |
| | DE 30 | DE 50 | DE 30 | DE 50 |
| 1 | 3.7 | 8.5 | | |
| 2 | 12.0 | 23.0 | | |
| 3 | 18.0 | 40.0 | | |
| 5 | 13.0 | 20.0 | 95 | 180 |
| 6 | 9.0 | 20.0 | | |

TABLE VII-continued

| Spasmolytic activity in vitro | | | | |
|---|---|---|---|---|
| | Spasmolytic activity | | | |
| Compound | Papaverinic type | | Atropinic type | |
| No. | DE 30 | DE 50 | DE 30 | DE 50 |
| 7 | 2.2 | 4.5 | 170 | 325 |
| 8 | 42.0 | 80.0 | 55 | 90 |
| 9 | 13.0 | 20.0 | | |
| 10 | 7.2 | 13.0 | | |
| 11 | 4.0 | 12.0 | | |
| 12 | 24.0 | 50.0 | 50 | 100 |
| 13 | 13.0 | 45.0 | 30 | 42 |
| 14 | 18.0 | 35.0 | 90 | 140 |
| 15 | 45.0 | 70.0 | 26 | 45 |
| 16 | 38.0 | 110.0 | 225 | 450 |
| 18 | 8.0 | 20.0 | 22 | 35 |
| 19 | 11.5 | 25.0 | | |
| 20 | 8.0 | 19.0 | 25 | 55 |
| 21 | 8.0 | 19.0 | 40 | 80 |
| 22 | 7.0 | 16.0 | | |
| 23 | 3.1 | 7.0 | 50 | 140 |
| 24 | 10.0 | 25.0 | 90 | 200 |
| 25 | 9.0 | 18.0 | 60 | 120 |
| 26 | 5.5 | 12.0 | 50 | 140 |
| 27 | 6.0 | 12.0 | | |
| 28 | 6.5 | 14.0 | 750 | 5000 |
| 29 | 4.0 | 8.5 | 45 | 100 |
| 30 | 6.0 | 13.0 | | |
| 31 | 16.0 | 28.0 | 40 | 65 |
| 32 | 4.5 | 9.5 | | |
| 33 | 4.0 | 8.5 | | |
| 34 | 8.0 | 16.0 | | |
| 36 | 8.5 | 20.0 | 14 | 28 |
| 37 | 6.8 | 13.0 | 50 | 80 |
| 38 | 6.0 | 16.0 | 95 | 200 |
| 39 | 43.0 | 80.0 | | |
| 41 | 4.3 | 10.5 | 24 | 46 |
| 42 | 3.5 | 17.0 | 190 | 300 |
| 43 | 7.0 | 25.0 | | |
| 44 | 5.5 | 8.0 | 30 | 70 |
| 45 | 14.0 | 27.0 | | |
| 46 | 2.5 | 10.0 | 6.5 | 18 |
| 47 | 9.0 | 15.0 | | |
| 48 | 6.0 | 25.0 | 10 | 18 |
| 49 | 1.6 | 3.7 | 21 | 28 |
| 50 | 5.0 | 12.0 | 48 | 70 |
| 51 | 3.5 | 6.5 | 61 | 95 |
| 52 | 8.0 | 14.0 | | |
| 53 | 4.5 | 8.0 | 75 | 140 |
| 54 | 9.5 | 12.0 | 52 | 90 |
| 55 | 3.5 | 7.5 | | |
| 56 | 10.0 | 16.0 | | |

3. Vasodilatatric activity a. The vaso-dialtatric activity with regard to the muscle fibre of vessels has been shown on the perfused isolated ear of the rabbit, after catheterism of the median artery, with the aid of a Tyrode solution maintained at ambient temperature.

The fall is registered with the aid of electronic apparatus including a Fleisch totalisator, the Tyrode solution being recovered at the ends of the "efferent" veins. It diminishes if one adds to the perfusion liquid a substance possessing vaso-constrictive properties such as adrenaline. The previous administration of a vaso-dilator opposes this diminution to an extent more or less marked according to the concentration used.

There has been observed, for certain of these derivatives, a vaso-dilatatric activity which, compared to that of papaverine hydrochloride, is of a similar intensity.

b. The vaso-dilatatric activity with regard to the coronary vessels has been shown on the isolated heart of the guinea-pig perfused according to the classic technique of LANGENDORFF, the coronary reduction being registered with the aid of electronic apparatus including a Fleisch totalisater.

There has been observed for certain derivatives selected by way of example a vaso-dilatatric activity comparable to that of papaverine hydrochloride. These derivatives equally oppose the vaso-constriction due to barium chloride added to the perfusion liquid.

4. Anti-serotonic activity

This has been researched in the rat by the technique of the acute oedema localised in the metatarsal region, provoked by the injection of 0.05 ml of a 0.01% solution of serotonine (sulphate of 5-hydroxy-tryptamine-creatinine) in an isotonic solution of sodium chloride.

The plethysmometric measurements of the paw having been subjected to the injection have been effected before, and at different times after, the injection of the serotonine.

The different results obtained with certain derivatives selected by way of example are presented in Table VIII and show a clear inhibition of the acute oedena localised consecutive to the intraplant injection of serotonine.

TABLE VIII

The derivatives to be studied have been administered by the oral route 30 minutes before the serotonine.

| Compound No. | Dose in mg/kg | Conc. g/100 ml of suspension | Average percentage reduction inoedema after 1 hour | 2 hours |
|---|---|---|---|---|
| 7 | 50 | 0.5 | 27.6 | 36.6 |
| 49 | 30 | 0.3 | 17.8 | 12.6 |
| 53 | 30 | 0.3 | 19.4 | 15.1 |
| | 50 | 0.5 | 40.6 | 42.9 |
| 54 | 30 | 0.3 | 22.4 | 16.0 |
| | 50 | 0.5 | 34.9 | 45.0 |
| 55 | 30 | 0.3 | 12.3 | 11.3 |
| | 50 | 0.5 | 40.7 | 39.8 |

5. Local anaesthetic activity

The method of MOUKHTAR has been chosen to show the activity of the derivatives studied on conduction anaesthesia (A. MOUKHTAR, C.R. Soc. Biol. 1909–66–187,189).

The reference local anaesthetic substance used in the tests has in each case been procaine hydrochloride in 0.5% solution in an 0.9% isotonic solution of NaCl. The three concentrations used to study the local anaesthetic activity of the new derivatives are 0.50, 0.25 and 0.10%, the vehicle being the isotonic 0.9% solution of NaCl.

The average anaesthetic activity of the substances chosen is expressed comparatively to that of the reference product chosen, by calculating the ratio of the average number *n* of the stimulations necessary to obtain the appearance of the skin reflex in the case of the derivatives studied, to the average number ($n'$) of the stimulation determined for the reference substance.

For example, in the experimental conditions defined above a substance possessing a local anaesthetic activity expressed by the number 1 has an activity equal to that of procaine hydrochloride.

The results obtained with certain selected compounds, by way of example, are indicated in Table IX and show a local anaesthetic activity comparable to that of procaine hydrochloride.

TABLE IX

The procaine hydrochloride and the derivatives studied are administered by the intradermal route at the rate of 0.20 ml per injection.

| Compound No. | concentration in g/100 ml of the derivative studied | concentration in g/100 ml of procaine hydrochloride | average number of stimulations for the derivative studied n | average number of stimulations for procaine hydrochloride n' | local anaesthetic activity n/n' |
|---|---|---|---|---|---|
| | 0.50 | 0.50 | 29.5 | 30.5 | 1.0 |
| 7 | 0.25 | 0.50 | 18.9 | 33.9 | 0.6 |
| | 0.10 | 0.50 | 12.2 | 36.0 | 0.3 |
| | 0.50 | 0.50 | 33.2 | 27.2 | 1.2 |
| 53 | 0.25 | 0.50 | 29.1 | 29.5 | 1.0 |
| | 0.10 | 0.50 | 14.2 | 30.5 | 0.5 |
| | 0.50 | 0.50 | 31.4 | 29.2 | 1.1 |
| 54 | 0.25 | 0.50 | 25.7 | 33.7 | 0.8 |
| | 0.10 | 0.50 | 16.7 | 28.2 | 0.6 |

The derivatives of β-[benzo(b)thienyl-3]-propionic acid can be used in human therapy and in veterinary therapy by reason of their spasmolytic, vasodilatatric, antiserotoninic and local anaesthetic properties.

The compounds which are particularly interesting in this regard are compounds Nos. 1, 5, 7, 11, 18, 23, 26, 32, 37, 46, 49, 50, 51, 53, 54, and 55 of Tables I to V.

The new drugs may be utilised in the treatment of spasmodic and painful conditions by digestive, biliary and urinary routes, of the arterio-venous system and the pelvic organs and in insufficient peripheral coronary and cerebral circulations.

The new derivatives may be presented for administration by oral, rectal or parenteral routes in man or animals, notably in association with excipients appropriate to these routes.

Thus, for example, they can be presented in the form of tablets, capsules, gelules, suppositories and injectable solutions. It will be understood that the invention includes pharmaceutical compositions which contain one or several of the new derivatives.

The daily dosage can, according to the case, vary from 50 to 600 mg.

| | |
|---|---|
| The citrate of the N,N-diethylamino propyl esters of α-allyl-β-[benzo(b)thienyl-3]propionic acid | 0.05 g |
| Lactose | 0.100 g |
| Starch | 0.095 g |
| Magnesium stearate | 0.005 g |
| to form a tablet weight 0.250 g. | |

We claim as our invention:

1. A β[-benzo (b) thienyl-3]-propionic acid derivative of the formula:

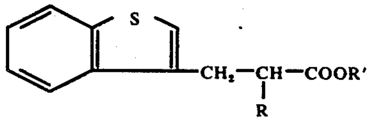

wherein R is selected from the group consisting of phenyl, benzyl, and thenyl; and R' is selected from the group consisting of $-(CH_2)_2-N(CH_3)_2$, $-(CH_2)_2-N(C_2H_5)_2$, 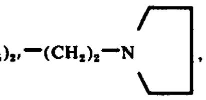,

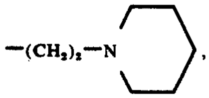, 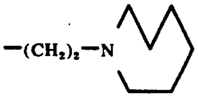, $-(CH_2)_3-N(CH_3)_2$, $-(CH_2)_3-N(C_2H_5)_2$,

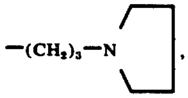, 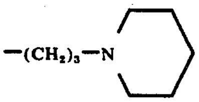 and

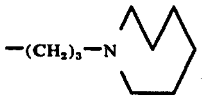

2. A derivative according to claim 1 in the form of an oxalic acid addition salt.

3. A derivative according to claim 1 in the form of a citric acid addition salt.

4. The β[-benzo (b) thienyl-3]-propionic acid derivative of claim 2 wherein R is phenyl.

5. The β[-benzo (b) thienyl-3]-propionic acid derivative of claim 1 wherein R is benzyl.

6. The β[-benzo (b) thienyl-3]-propionic acid derivative of claim 1 wherein R is thenyl.

* * * * *